United States Patent [19]

Brown

[11] 4,427,439
[45] Jan. 24, 1984

[54] COMPOSITION FOR PLANT GROWTH REGULATION

[75] Inventor: Michael J. Brown, Randolph, N.J.

[73] Assignee: GAF Corporation, New York, N.Y.

[21] Appl. No.: 144,502

[22] Filed: Apr. 28, 1980

[51] Int. Cl.³ .................... A01N 43/40; A01N 43/36
[52] U.S. Cl. ........................................ 11/94; 71/72; 71/76; 71/95; 71/103
[58] Field of Search .................... 71/95, 103, 72, 94, 71/76

[56] References Cited

U.S. PATENT DOCUMENTS

| | | | |
|---|---|---|---|
| 3,830,838 | 8/1974 | Kollmeyer et al. | 71/103 |
| 3,885,951 | 5/1975 | Hofer et al. | 71/72 |
| 4,134,752 | 1/1979 | Pilgram et al. | 71/103 |
| 4,191,555 | 3/1980 | Kliegman | 71/95 |
| 4,227,918 | 10/1980 | Hofer et al. | 71/103 |

OTHER PUBLICATIONS

Takahashi et al., "Long-Lasting Pyrethroid, etc." (1975) CA84 No. 85633v, (1976).
Laden, "Pharmaceutical Compositions, etc." (1969) CA73 No. 102083d, (1970).
Halliday, "Solvent System for Formulating etc." (1971) CA75 No. 109261k, (1971).
Kukalenko et al, "Pyrrolidinone ders., etc." (1973) CA79 No. 39335u, (1973).

*Primary Examiner*—Glennon H. Hollrah
*Attorney, Agent, or Firm*—Marilyn J. Maue; J. Gary Mohr; Joshua J. Ward

[57] ABSTRACT

This invention relates to a composition comprising a mixture of a N-heterocyclic amide, such as N-methylpyrrolidone, and a 2-haloethylsulfinamide having from 3 to 16 carbon atoms for the treatment of plants, including trees, shrubs, farm crops and ornamentals to achieve promotional and sustained hormonal ethylene plant growth regulatory effects; and the method of using said composition.

19 Claims, No Drawings

COMPOSITION FOR PLANT GROWTH REGULATION

The present invention is particularly directed to the promotion and extension of high activity in the plant growth response to haloethylsulfinamides of the general type disclosed in British Pat. No. 1,397,450; the entire teaching of which, with respect to 2-haloethylsulfinamides, is incorporated herein by reference. Accordingly, it is an object of the present invention to provide an interacting multicomponent composition for sustaining and increasing plant response to said sulfinamide compounds, particularly beneficial in the treatment of seeds to promote germination and development through the seedling stage to harvestability for various plants of the Citrus, Solanaceae, Musaceae, Malvaceae, Leguminosae, Gramineae, Rubiocease, Euphorbiaceae, Rubus and Rosaceae classes including such species as cereal grasses, corn, beans, tomatoes, bananas, cotton, oranges, apples, roses, raspberries and many others responsive to hormonal ethylene effects such as advancement of crop maturation and defoliation, development of shorter, sturdier plants having increased fruit set sites and hastening of fruit ripening.

Another object is to provide the above advantages while simultaneously reducing plant susceptability to lodging.

Still another object is to provide an ecologically safe composition for the treatment of plants and an economical method for its application.

These and many additional objects and advantages will become apparent from the following description and disclosure.

According to this invention, there is provided an interacting mixture for preharvest or postharvest treatment of a plant, plant part or plant situs which comprises as active ingredients, a N-heterocyclic amide having one hetero-nitrogen atom and 4 or 5 carbon atoms in a 5 or 6 membered ring, such as for example, N-methylpyrrolidone or polyvinylpyrrolidone, and a sulfinamide capable of generating ethylene, having the formula:

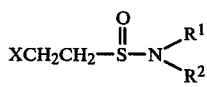

wherein X is a chlorine or bromine atom; $R^1$ is hydrogen or methyl; and $R^2$ is hydrogen, phenyl, benzyl, alkyl having from 1 to 12 carbon atoms, alkenyl of 2 to 6 carbon atoms or an alkylene pyrrolidonyl radical of from 5 to 8 carbon atoms.

Examples of suitable N-heterocyclic amides include N-methyl-2-pyrrolidone, 2-pyrrolidone, polyvinylpyrrolidone having from 2 to 5,000 monomer units, N-methyl-2-pyridone, N-methyl-2-piperidone, N-methyl-2,5-succinimide, succinimide, N-(o-tolyl)-2-pyrrolidone, N-(2-hydroxyethyl)-2-pyrrolidone, and isomers and mixtures of these amides with other heterocyclic amides or with linear amides such as the methyl substituted acetamide or formamide, e.g., dimethyl acetamide, methyl acetamide and methyl formamide or amines. Of these amide components, the tertiary heterocyclic amides are preferred and N-methylpyrrolidone is most preferred.

It has now been discovered that a N-heterocyclic compound of this invention, when combined with the above described sulfinamides significantly increases the amount of ethylene generation and metabolic growth promotional activity over a longer duration than would be obtained with sulfinamide per se. This result is wholly, unexpected since, except for moderate defoliation, the N-heterocyclic compounds had been regarded as inert solvents or dispersants for water-soluble compounds and have been shown to have no metabolic plant growth regulating properties when employed in mixtures. Accordingly, it would be expected that the addition of such heterocyclics to a highly active plant growth promoter would have no promotional effect on ethylene generation or any sustaining influence on growth regulation. Instead it is found that the promotional effects of the above sulfinamide compounds are significantly extended and increased. However, no promotional effect from the present N-heterocyclic compounds is derived from their combination with alkylthiophthalimides or trifluoromethyl toluidide substituted 2-haloethylsulfinamides.

The sulfinamides of the present invention include the methyl, ethyl, propyl, isopropyl, butyl, isobutyl, pentyl, isopentyl, hexyl, isohexyl, cyclohexyl, 1,2-dimethylbutyl, 4,4-dimethybutyl, heptyl, octyl, 2,4,6,7-tetramethyloctyl, nonyl, decyl, dodecyl, chloroethyl, bromoethyl, 2,3-dibromobutyl, 1,3-dichlorobutyl, allyl, phenyl, benzyl, octenyl, 2,4,6-trichloroctenyl-4, etc. amides of a 2-haloethyl sulfinic acid. Of these, the unsubstituted 2-bromo- or 2-chloro- ethylsulfinamide, the N-methyl-N-phenyl-, the N-alkyl-, the N-phenyl- and the N-benzyl- 2-haloethylsulfinamides are preferred.

Generally, the $C_5$ to $C_{12}$ N-alkyl substituted amides are most active of the alkyl groups for promotion of ripening; whereas the $C_1$ to $C_8$ are more active for promotion of abscission.

The following discussion is directed to the preferred mixture, involving N-methyl-2-pyrrolidone and a 2-haloethylsulfinamide however it is to be understood that any of the other N-heterocyclic compounds described above or their mixtures with other N-heterocyclic amides or with linear methyl substituted amides such as dimethylacetamide, methyl formamide, methylacetamide can be substituted in the following discussion or in the examples to provide the benefits described.

The proportion of N-methylpyrrolidone to 2-haloethylsulfinamide employed in the present invention can vary between about 0.05:1 and about 5:1, preferably between about 0.5:1 and about 3:1. For economy and for more uniform coverage, the mixture or the individual components thereof are incorporated in a conventional inert carrier or diluent which is conveniently a liquid selected from the group comprising water, a methyl substituted benzene, cyclohexane and other higher boiling paraffins, vegetable or mineral oil or oil fraction such as a petroleum oil fraction, a fatty alcohol or ketone such as acetone or methyl ethyl ketone (MEK) or any compatible mixture of the above. Of these, water is the most desirable because of its availability; although when the sulfinamide portion of the mixture is in high excess, a surfactant or emulsifier is advantageously added to the composition. Such adjuvants, when employed, comprise between about 0.001% and about 20% of the sulfinamide component. Although any of the usual inert emulsifiers or surfactants can be employed, particularly recommended are the nonionics and anionics such as polyethylene- or polypropylene- glycols, polyoxyethylene- or polyoxypropylene- glycols, polyoxyethylene- or polyoxypropylene- ethers, alkyl or aryl sulfates or sulfonates, lignin, methyl cellulose, etc. The present compositions with carrier generally contain from about 0.005% (50 ppm) to about 2% (20,000 ppm), preferably from about 0.01% to about 0.8% of the active mixture. As a liquid formulation, the mixture with liquid carrier can be employed as a solution, an emulsion or dispersion. The formulation can also contain other adjuvants such as a thickening agent, e.g. any of the conventionally employed gums or resins including locust bean gum, low molecular weight polymers, etc. for application in areas of high rainfall.

It is to be understood, however, that the present mixture can also be applied to a plant, plant part or plant situs as a paste, as a powder or as a course granulated solid by the use of such dry extenders as talc, bentonite clay, sand, diatomaceous earth, kaolin, petrolatum pastes or jellies or other standard extenders. The concentration of the mixture in these extenders is substantially the same as recited above for liquid carriers.

In general, the concentration of N-methylpyrrolidone in the mixture with respect to the plant or plant part can vary within a wide range between about 10 ppm and about 10,000 ppm, preferably between about 75 ppm and about 3,000 ppm, depending on the effect desired, the plant treated, the climatic conditions at the time of application and the maturity of the plant.

The formulations or compositions of the present invention can be prepared by any one of several convenient methods. For example, the sulfinamide and the N-heterocyclic amide can each be separately dissolved in, or admixed with, the same or different solvents or carrier and then combined before applying to the plant, plant part or plant situs or the componetns in the same or individual carrier can be combined upon application to the plant. Alternatively, both components can be simultaneously or sequentially dissolved in, or admixed with the same carrier or solvent and cosolvent to provide the desired composition. adjuvants can be added to either component-carrier composition, before or after combination of the componens. In certain instances it may be desirable to form a composition with a liquid carrier for one of the components, e.g. an aqueous solution of N-methylpyrrolidone, and a second composition with a dry carrier for the remaining component, after which the components may be mixed to form a paste or viscous liquid which is resistant to removal by rain or such subsequent treating operations as the consumer may require, eg. the separate application of a fungicidal, a selective herbicidal, pesticidal or defoliant spray.

The present formulations may also contain an additional plant growth regulating compound or composition and/or other agricultural chemicals such as a fungicide, nematocide or pesticide or combinations of these, provided that the additives do not materially alter the activity of the present mixture.

The above compositions or formulations are applied to a plant, a plant part or the situs from which seedlings will emerge by spraying, dusting, atomizing, broadcasting, immersing or washing as convenient for the particular operation. Generally, plant dosage levels between about 0.0005 and about 0.5 gram, more desirably between about 0.003 and about 0.1 gram, per plant of N-methylpyrrolidone in the above mixture is applied to obtain the increased and sustained activity of the sulfiamide compound. The plant is contacted with the present mixture at a rate of form about 0.1 to about 100 kg per hectare, more usually form about 1 to about 100 kg per hectare of soil area.

By way of illustration, in the preharvest treatment of cotton the present mixture of components is applied prior to harvest and after boll set, for example application of from about 200 ppm to about 5,000 ppm of mixture in a carrier is preferably effected at least 30 days after square set; although it is to be understood that application can be made at any time after square set up through initial boll brak without causing any damage to the plant or plant fiber.

The advantages realized form application of the present composition in the preharvest treatment of cotton are enumerated as follows.

1. Providing a composition for effecting rapid boll ripening, boll dehiscence and leaf defoliation so as to avoid the need for multiple chemical applications.
2. Increasing the rate of immature boll dehiscence so as to provide more uniformly opened bolls for first harvest collection and synchronizing defoliation so that it is effected when the bolls are fully developed and opening or opened.
3. Providing coaction between the active ingredients of the composition to produce metabolic ethylene effects in increasing dehiscence.
4. Advancing early dehiscence of bolls containing mature fibers while having substantially no effect on the completely matured breaking bolls so as to increase the proportion of recoverable cotton in a single, first harvest and to minimize and/or obviate the necessity of a second harvest.
5. Providing cotton fiber of inherent high quality.
6. Reducing plant temperature sensitivity and resistance to low temperature dehiscence.
7. Permitting later planting of crop and/or earlier harvesting.
8. Providing economic and labor saving harvest of cotton.

In the case of soybeans and cereal grasses, the present mixtures promote shorter sturdier stems and offer extended protection against lodging. These mixtures also prevent excessively rapid defoliation so as to conserve transpiration as the underdeveloped crop matures to harvestability. To obtain these beneficial effects, between about 500 and about 3,000 ppm of a 1:2 to 2:1 molar mixture of N-methyl pyrrolidone/sulfinamide such as 2-bromoethyl sulfinamide, N-phenyl-2-chloroethylsulfinamide or N-hexyl-2-chloroethylsulfinamide, was sprayed to drench on plants in the fifth trifoliate leaf stage. Omission of N-methylpyrrolidone in the composition results in rapid defoliation before 80% of the crop has reached maturity and taller, thinner plant stems were produced which resulted in a significant increase in lodging; whereas the present admixtures overcome lodging and delay defoliation by several days while advancing the crop to ripeness at least 4 to 5 days sooner than untreated crop.

As an example of ripening of picked fruit, 300–400 ppm N-methylpyrrolidone is added to each of 500–600 ppm aqueous solutions of 2-chloroethylsulfinamide, N-benzyl-2-bromoethylsulfinamide and N-octyl-2-chloroethylsulfinamide containing 1% methyl ethyl ketone. A fourth aqueous solution containing 900 ppm 2-chloroethylsulfinamide omitting N-methyl pyrrolidone is also prepared. Three green picked bananas from the same stalk are immersed in each of the four solutions for a period of 35 minutes. The fruit treated with the solution free of N-methylpyrrolidone, i.e. the fourth solution, yellows 5 days before untreated fruit; whereas the bananas treated with the remaining three solutions yellow 6 to 7 days before untreated fruit.

When used alone, the N-heterocyclic compounds of the present invention behave as ethylene inhibitors as shown by the following examples 1-19 and fruit yellowing is significantly delayed 1 or 2 days after normal yellowing. Accordingly, it is all the more surprising that these compounds induce a promotional ethylene generating effect when combined with the present sulfinamides. In accordance with the following Examples 1-19, the ethylene inhibiting effect of various N-heterocyclic amides is measured and reported in Table I.

EXAMPLES 1-19

In a growth chamber maintained at 30° C. and 2,000–3,000 foot candle light, soybean plants from the same seed source were grown to various stages of development. Each of the following experiments were carried out in quadruplicate, and the results (found to be highly reproducible), were averaged and reported in Table I below.

In the following Examples 1-19, leaf disc samples from (a) plant seedlings about 2 weeks old (Examples 1-4); (b) underdeveloped plants at the trifoliate stage (Examples 5-8); (c) fully developed plants with no further growth increase (Examples 9-12); (d) a second group of fully developed plants (Examples 13-16); and (e) a third group of fully developed plants (Examples 17-19), were removed by cutting the leaf with a circular cork borer. Each leaf disc sample was immersed for 30 minutes in a 100 milliter aqueous solution containing water as a control or aqueous solutions containing 1,000 ppm and 3,000 ppm of the compound to be tested. At the end of 30 minutes the leaf disc was removed from its solution, patted dry and inserted into a 25 ml glass vial equipped with a septum through which a syringe could be inserted for extracting a sample of the supernatant air above the leaf disc. Examples 1 through 16 were allowed to stand in the light for one hour and Examples 17 through 19 were allowed to stand in the light for 16 hours, after which a gas sample above the leaf in the vial was removed and analyzed for ethylene by gas liquid phase partition chromatography. Comparison with the control, reported in nanoliters of ethylene per liter of air per 10 $cm^2$ of leaf surface, are presented in the following Table (based on an average of 4 replicate samples). For the purpose of comparison, the control was assigned a value of 1.0 and the test compounds we reported as the percent deviation from the control.

Each of the foregoing experiments was repeated, except that the leaf disc samples were similarly treated and held in the dark for the above period prior to analysis of the gas samples. The results of these experiments are also reported in Table I.

TABLE I

| Ex. No. | TEST COMPOUND | $C_2H_4$ GENERATED BASED ON CONTROL | | | |
|---|---|---|---|---|---|
| | | 1000 ppm | | 3000 ppm | |
| | | Light | Dark | Light | Dark |
| 1. | Control(water) = 500 nl $C_2H_4$/ 1/10 $cm^2$ | 1.0 | 1.0 | 1.0 | 1.0 |
| 2. | N—(hydroxyethyl)-2-pyrrolidone | −38% | −25% | −45% | −32% |
| 3. | 2-Pyrrolidone | −73% | −69% | −78% | −75% |
| 4. | N—methyl-2-pyrrolidone | −84% | −82% | −91% | −91% |
| 5. | Control(water) = 640 nl $C_2H_4$/ 1/10 $cm^2$ 10 $cm^2$ | 1.0 | 1.0 | 1.0 | 1.0 |
| 6. | N—methyl-2-piperidone | −38% | −60% | +150% | +110% |
| 7. | N—methyl-2-pyridone | −50% | −55% | +130% | +115% |
| 8. | N—methyl-2-pyrrolidone | −50% | −65% | −65% | −90% |
| 9. | Control(water) = 640 nl $C_2H_4$/ 1/10 $cm^2$ | 1.0 | 1.0 | 1.0 | 1.0 |
| 10. | N—(hydroxyethyl)-2-pyrrolidone | −15% | +120% | +185% | +250% |
| 11. | 2-pyrrolidone | −40% | −24% | +120% | +166% |
| 12. | N—methyl-2-pyrrolidone | −50% | −50% | −61% | −60% |
| 13. | Control(water) = 640 nl $C_2H_4$/ 1/10 $cm^2$ evolved/10 $cm^2$ | 1.0 | 1.0 | 1.0 | 1.0 |
| 14. | N—methyl-2-pyrrolidone | −50% | −60% | −20% | −40% |
| 15. | N—(methyl)-2-piperidone | +40% | −50% | +190% | — |
| 16. | N—methyl-2-pyridone | −80% | −50% | −40% | +170% |
| 17. | Control(water) = 500 nl $C_2H_4$/ 1/10 $cm^2$ evolved/10 $cm^2$ | 1.0 | — | 1.0 | — |
| 18. | 2-pyrrolidone | −40% | — | +104% | — |
| 19. | N—methyl-2-pyrrolidone | −50% | — | −46% | — |

It is noted that certain of the heterocyclic agents in the above table provide an ethylene generating effect at the higher 3,000 ppm concentration and that this effect occurs in older plant tissue which has less tolerance for excessive amounts of certain N-heterocyclic amides and therefore an increase marked by the generation of ethylene is observed as the response to a stress effect induced by the chemical. In these cases, it is also noted that the agent generally reaches an efficacy threshold at a concentration less than 3,000 ppm, e.g. 1,000–2,000 ppm. Specifically, at between about 1,800–2,400 ppm, a maximum response is obtained and amounts in excess of about 2,000 ppm are unable to provide additional inhibition of ethylene; in fact, concentrations of 3,000 ppm often induce a stress situation where the opposite result, namely increased ethylene generation, is observed. Accordingly, with the exception of 2-pyrrolidone, N-methyl pyrrolidone and polyvinylpyrrolidone, the selection of the amide component in the present mixture is partly dependent on the age of the plant.

The addition of equimolar amounts of any of the above heterocyclic amides or polyvinylpyrrolidone significantly increases the initial young plant response to the 2-chloroethylsulfinamides, or the 2-bromoethylsulfinamides of this invention, in solution eg. a 10% aqueous alcoholic solution, containing from about 500 to about 1,800 ppm by at least 20% and higher, depending on the amide employed. On fully matured plant tissue the enhancing effect for these amides is at least 5%.

Sustained activity of the sulfinamide plant growth regulant is observed in the dehiscence of cotton bolls and ripening of fruit, which responses are typical hormonal effects of ethylene generation. Specifically, a group of untreated 12-week old hirsuiti cotton plants exhibit a 75% normal boll opening at 45 to 60 days after square set. When spraying hirsuiti cotton crop 15 days after square set with 1,000 ppm N-heptyl-2-chloroethylsulfinamide in aqueous solution, 75% of the bolls are opening after 10 days, and 85% are opened after the 12th day. Upon addition of 800 ppm N-methyl-2-pyrrolidone to the sulfinamide solution, 85% of the bolls are opened on the 10th day after spraying and, by the 12th day, the number of opened bolls is increased to 95–100%.

It is also noted that cotton, tomato and pea plants sprayed with the present mixtures in a concentration of 500–1,000 ppm have a shorter more branching structure offering more crop sites than the corresponding untreated or sulfinate acid treated plants. Other plant growth ethylene responses are also enhanced by treatment with the present mixtures, particularly the effects of ripening, abscission, promotion of seed germination and rhizome sprouting.

Promotion of seed germination with the present mixtures is effected at lower dosage levels, e.g. 100 to 500 ppm of mixture wherein amide: sulfinamide mole ratio is between about 0.05:1 and about 1:1. By way of example 150 ppm aqueous solutions of ethephon, 2-chloroethylsulfinamide and 2-chloroethylsulfinamide/2-pyrrolidone in a 1:0.3 mole ratio are compared for promotion of wheat seed germination after treating 3 separate humidity and temperature controlled plots containing 100 seeds each with 1.5 liter of each solution. An additional plot is reserved as a control. After 10 days, the control plot provided only 25% germination, the ethephon treated plot produced 55% germination; the sulfinamide treated plot achieved about 85% germination and the plot treated with the present mixture provided 87% germination.

EXAMPLES 20 THROUGH 24

Comparison of Plant Growth Regulants on In Vivo Production of Ethylene is Soybean Leaf Tissue Twenty leaf discs, cut with a 1.76 cork borer from soybean plants grown to the unifoliate leaf stage in a greenhouse maintained at 26°–30° C., on a 16 hour photoperiod, were floated on 25 ml of aqueous solutions in a closed Petri dish. The aqueous solutions contained 1000 ppm of compound to be tested and 4 discs were floated in each solution, including one water solution to serve as control. After floating on the solutions for 30 minutes the discs were removed, blotted dry with paper towelling, and the four discs from each solution were placed in a separate 8 ml vial fitted with a septum through which the internal atmosphere of each vial could be sampled by insertion of a 1 ml syringe. Four replicate vials were thus prepared for each treatment. The vials were allowed to stand in light for 1 hour, and then stored in the dark for 16 hours after which gas samples were withdrawn and analyzed by gas-liquid chromatography. The averaged results of the analyses for the different compounds are reported as nannoliters of ethylene per liter of atmosphere per $cm^2$ of leaf sample per mmole of test compound in the following Table 2.

TABLE 2

| Example No. | Compound | nl $C_2H_4$/l/$cm^2$/mmole |
|---|---|---|
| 20. | Control | 114.7 |
| 21. | $ClC_2H_4\overset{O}{\underset{\|\|}{S}}NH_2$ | 21,568 |
| 22. | $ClC_2H_4\overset{O}{\underset{\|\|}{S}}NH(CH_2-N{\supset}O)$ | 29,554 |
| 23. | Equimolar mixture of chloroethylsulfinbutyrate and the compd. of Ex. 21 + NMP (1:1 molar) | 80,500 |
| 24. | Compd. of Ex. 22 + NMP (1:1 molar) | 32,836 |

NMP = N—methyl-2-pyrrolidone

When the above solutions of examples 23 and 24 are individually sprayed on 3 groups of 10 soybean plants growing in a greenhouse, the fruit ripened in both cases at least 10 days before untreated control, plants; thus, the rate of ripening is found to be directly proportional to the amount of ethylene generated.

EXAMPLES 25 THROUGH 29

Branches on one quarter of Florida lemon trees, drenched with 1,000 ppm aqueous solutions of 1:1 molar N-methyl-2-pyridone/N-substituted 2-haloethylsulfinamides caused abscission of leaves and some fruit. Within one week after treatment, the leaves became brittle and dehydrated and within 3 weeks considerable leaf abscission occurred as shown in the following Table 3. Abscission form the untreated shielded portion of the trees was also noted; although this defoliation is somewhat higher, due to systemic effect, than normal defoliation from wholly untreated trees.

TABLE 3

| Example No. | Sulfinamide | % Leaf abscission from tree |
|---|---|---|
| 25 | Untreated Branches, Same tree | 20–30% |
| 26 | N—butyl-2-bromoethylsulfinamide | 50–60% |
| 27 | N—phenyl-2-bromoethylsulfinamide | 55–70% |
| 28 | N—cyclohexyl-2-bromoethylsulfinamide | 45–55% |
| 29 | N—ethyl-2-chloroethylsulfinamide | 60–70% |

EXAMPLES 30 THROUGH 40

Groups of 6 green picked New Yorker Tomatoes, after immersion for 1.5 hours in 800 ppm aqueous solutions of 1:3 molar N-methyl-2-pyrrolidone/2-haloethylsulfinamides, are reddened to ripeness. A second series of 6 green picked New Yorker tomatoes are similarly treated except that N-methyl-2-pyrrolidone is eliminated from the solution which comprises 800 ppm of the 2-haloethylsulfinamide. A final group of 6 green picked New Yorker tomatoes is left untreated for comparison purposes. The result of tomato reddening are shown in following Table 4.

TABLE 4

| Example No. | Sulfinamide* | \% Reddened Days After Treatment | | | |
|---|---|---|---|---|---|
| | | 4 | 6 | 8 | 10 |
| 30 | untreated | 5 | 15 | 40 | 50 |
| 31 | N—benzyl-2-chloroethylsulfinamide | 30 | 65 | 80 | 90 |
| 32 | N—phenyl-2-chloroethylsulfinamide | 20 | 50 | 70 | 85 |
| 33 | 2-bromoethylsulfinamide | 15 | 35 | 63 | 60 |
| 34 | N,N—methyl-phenyl-2-chloroethyl sulfinamide | 45 | 75 | 85 | 90 |
| 35 | N,N—ethyl-phenyl-2-bromoethyl sulfinamide | 25 | 50 | 65 | 70 |
| 36 | Compd. of Ex. 31/NMP | 40 | 75 | 85 | 100 |
| 37 | Compd. of Ex. 32/NMP | 40 | 65 | 75 | 90 |
| 38 | Compd. of Ex. 33/NMP | 30 | 50 | 70 | 80 |
| 39 | Compd. of Ex. 34/NMP | 50 | 80 | 90 | 95 |
| 40 | Compd. of Ex. 35/NMP | 45 | 60 | 80 | 90 |

EXAMPLES 41 THROUGH 49

Promotion of Seed Germination

Eight groups of 20 sunflower seeds from the same seed source at the same stage of development are separately immersed for 1.5 hours in separate aqueous 10% methanol solutions each containing 5% polyoxyethylene glycol surfactant and 150 ppm of a different plant growth regulating agent as defined in Table 5. An additional solution containing no plant growth regulating agent is provided as a control in which 20 additional seeds are immersed for the same period. The number of seeds germinated for each treatment 5 days after immersion when planted in flats and exposed to standard light and humidity conditions in a greenhouse, is shown below.

TABLE 5

| | Active Regulant | Seed Germination % |
|---|---|---|
| 41 | N—Isopropyl-2-chloroethylsulfinamide | 15 |
| 42 | N—methyl-N—benzyl-2-chloro-sulfinamide | 15 |
| 43 | N—Cyclohexyl-2-chloroethylsulfinamide | 13 |
| 44 | N—decyl-2-bromoethylsulfinamide | 14 |
| 45 | None | 4 |
| 46 | Compound of 41 + NMP (1:1 molar mix) | 16 |
| 47 | Compound of 42 + NMP (1:1 molar mix) | 17 |
| 48 | Compound of 43 + NMP (1:1 molar mix) | 16 |
| 49 | Compound of 44 + NMP (1:1 molar mix) | 17 |
| 50 | Compound of 43 + 2-methylsuccinimide (1:1 molar mix) | 16 |

The above represent preferred examples involving the use of the present compositions. However, it is to be understood that any of the other N-heterocyclic amides defined in the foregoing disclosure, particularly 2-pyrrolidone, and polyvinyl-pyrrolidone K30 to K90, as well as any of the other haloethyl sulfinamides described herein can be substituted in the above examples 23, 24, 26–29, 36–40 and 46–49 to provide the benefits described therein.

What is claimed is:

1. A coacting plant growth regulating, ethylene generating composition consisting essentially of a 2-haloethylsulfinamide having the formula:

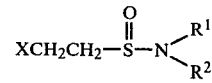

wherein X is a chlorine or bromine atom; $R^1$ is hydrogen or methyl and $R^2$ is hydrogen, phenyl, benzyl or alkyl having from 1 to 12 carbon atoms or $R^1$ and $R^2$ together with the nitrogen atom form a pyrrolidonyl ring and a N-heterocyclic amide selected from the group consisting of N-methylpyrrolidone, pyrrolidone, N-methyl pyridione, polyvinylpyrrolidone and N-methyl succinimide combined in a mole ratio of between about 1:0.05 and about 1:5.

2. The composition of claim 1 wherein the mole ratio of said 2-haloethylsulfinamide to said N-heterocyclic amide is between about 1:0.3 and about 1:3.

3. The composition of claim 2 wherein said sulfinamide is a 2-chloroethylsulfinamide.

4. The composition of claim 3 wherein said sulfinamide is N-methyl-N-phenyl-2-chloroethylsulfinamide.

5. The composition of claim 3 wherein said sulfinamide is N-cyclo-hexyl-2-chloroethylsulfinamide.

6. The composition of claim 3 wherein said sulfinamide is N-pyrrolidonyl-2-chloroethylsulfinamide.

7. The composition of claim 2 wherein said sulfinamide is 2-bromoethylsulfinamide.

8. The composition of claim 3 wherein said sulfinamide is N-phenyl-2-chloroethylsulfinamide.

9. The composition of claim 2 wherein said sulfinamide is N-phenyl-2-bromoethylsulfinamide.

10. The composition of claim 2 wherein said sulfinamide is N-cyclo-hexyl-2-briomoethylsulfinamide.

11. The composition of claim 2 wherein said N-heterocyclic amide is N-methyl-2-pyrrolidone.

12. The composition of claim 2 wherein said N-heterocyclic amide is 2-pyrrolidone.

13. The composition of claim 2 wherein said N-heterocyclic amide is N-methyl pyridone.

14. The composition of claim 2 wherein said N-heterocyclic amide is N-methyl succinimide.

15. The process of producing enhanced hormonal ethylene response in a plant or plant part by contacting a plant, plant part or plant situs with an effective amount of the coacting mixture of claim 1.

16. The process of producing enhanced hormonal ethylene response in a plant or plant part by contacting the plant, plant part or plant situs with the coacting mixture of claim 2.

17. The process of claim 15 wherein the coacting mixture is extended by an inert carrier to form a composition and the concentration of the coacting mixture in said composition is between about 50 ppm and about 15,000 ppm.

18. The process of claim 17 wherein the composition is applied to the plant as an aqueous spray.

19. The process of claim 17 wherein the composition additionally contains a thickener.

* * * * *